United States Patent [19]

Fuchs et al.

[11] Patent Number: 4,748,257
[45] Date of Patent: May 31, 1988

[54] 4-FLUORO-3-PHENOXY-BENZALDEHYDE ACETALS

[75] Inventors: Rainer Fuchs; Fritz Maurer, both of Wuppertal; Uwe Priesnitz, Unna-Massen; Hans-Jochem Riebel, Wuppertal; Erich Klauke, Odenthal, all of Fed. Rep. of Germany

[73] Assignee: Bayer Aktiengesellschaft, Leverkusen, Fed. Rep. of Germany

[21] Appl. No.: 887,471

[22] Filed: Jul. 21, 1986

Related U.S. Application Data

[60] Division of Ser. No. 303,657, Sep. 18, 1981, Pat. No. 4,626,601, which is a continuation of Ser. No. 174,762, Aug. 4, 1980, abandoned.

[30] Foreign Application Priority Data

Aug. 22, 1979 [DE] Fed. Rep. of Germany ....... 2933979

[51] Int. Cl.$^4$ .................. C07D 317/16; C07C 43/303
[52] U.S. Cl. ................... 549/453; 549/374; 549/347; 568/592
[58] Field of Search ...................... 549/453, 374, 347; 568/592

[56] References Cited

U.S. PATENT DOCUMENTS 3,904,654 9/1975 Birum .................. 549/453
3,965,127 6/1976 Birum .................. 549/453

Primary Examiner—Nicky Chan
Attorney, Agent, or Firm—Sprung Horn Kramer & Woods

[57] ABSTRACT

The new compound

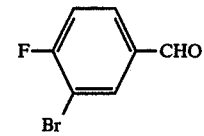

is prepared and converted to the new acetal

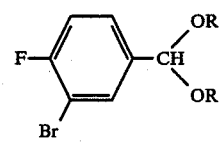

which is reacted with an alkali phenolate or alkaline earth metal phenolate in the presence of copper or a copper compound as a catalyst and in the presence of a diluent at a temperature between about 100° and 200° C. to produce the new acetal

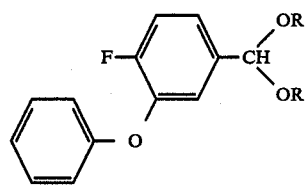

which can be hydrolyzed to the corresponding aldehyde which is a known intermediate for pyrethroid-like insecticides.

2 Claims, No Drawings

4-FLUORO-3-PHENOXY-BENZALDEHYDE ACETALS

This is a division of application Ser. No. 303,657, filed Sept. 18, 1981, now U.S. Pat. No. 4,626,601, which is in turn a continuation of Ser. No. 174,762, filed Aug. 4, 1980, now abandoned.

The invention relates to certain new 4-fluoro-3-phenoxy-benzaldehyde acetals, to an unobvious process for their preparation and to 3-bromo-4-fluoro-benzaldehyde, which is new, and acetals thereof and to preparative processes for these compounds.

It is known that 4-fluoro-3-phenoxy-benzaldehyde, an intermediate product for pesticidally active pyrethroids, is obtained when 4-fluoro-3-phenoxy-benzyl bromide is reacted with hexamethylenetetramine and the product of this reaction is heated with acids (see DE-OS (German Published Specification) No. 2,709,264). However, the yields in this synthesis method and also in the preparation of the starting compound from 4-fluoro-3-phenoxy-toluene and N-bromo-succinimide are unsatisfactory.

The present invention now provides:

(1), as new compounds, the 4-fluoro-3-phenoxy-benzaldehyde acetals of the general formula

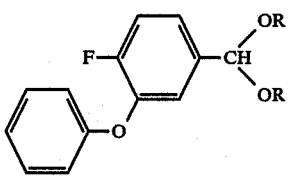

in which
the two radicals R individually represent alkyl or together represent alkanediyl (alkylene);

(2) a process for the preparation of a compound of the formula (I), characterized in that a 3-bromo-4-fluoro-benzaldehyde acetal of the general formula

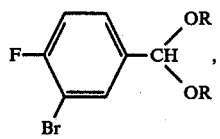

in which
R has the meaning indicated above,
is reacted with an alkali metal phenolate or alkaline earth metal phenolate in the presence of copper or a copper compound as a catalyst and in the presence of a diluent, and if appropriate in the presence of an auxiliary selected from alkali metal halides and carbonates and alkaline earth metal halides and carbonates, and if appropriate in the presence of a basic dehydrating agent, at a temperature between about 100° and 200° C.;

(3) the use of the compounds of the formula (I) as intermediate products for the preparation of 4-fluoro-3-phenoxy-benzaldehyde by reaction with acids by known methods for splitting acetals;

(4), as new compounds, 3-bromo-4-fluoro-benzaldehyde acetals of the general formula

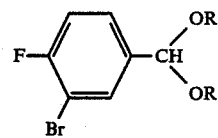

in which
the two radicals R individually represent alkyl or together represent alkanediyl (alkylene);

(5) a process for the preparation of a compound of the formula (II), characterized in that 3-bromo-4-fluoro-benzaldehyde, of the formula

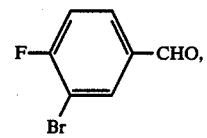

is reacted with an alkanol or alkanediol, if appropriate in the presence of a catalyst and/or a water-binding agent, and if appropriate using a diluent, at a temperature between about 0° and 150° C.;

(6), as a new compound, 3-bromo-4-fluoro-benzaldehyde, of the formula

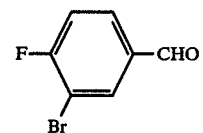

and (7) a process for the preparation of 3-bromo-4-fluoro-benzaldehyde, characterized in that a 3-bromo-4-fluoro-benzene of the general formula

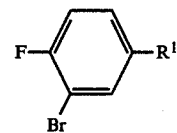

in which
$R^1$ represents $CH_3$ or $-CH_2-OH$,
is converted into the aldehyde in the customary manner.

Surprisingly, 4-fluoro-3-phenoxy-benzaldehyde can be prepared in a simpler manner and in a better yield via the abovementioned new intermediate products than by the abovementioned known process.

Formula (I) provides a definition of the new 4-fluoro-3-phenoxy-benzaldehyde acetals. Preferably, in this formula,
the radicals R individually represent $C_1$–$C_4$-alkyl or together represent $C_2$–$C_5$-alkanediyl, especially $-CH_2-CH_2-$.

If 3-bromo-4-fluoro-benzaldehyde propyleneacetal and potassium phenolate are used as starting compounds, the process described under (2) for the preparation of the new 4-fluoro-3-phenoxy-benzaldehyde acetals ("process (2)") can be outlined by the following equation:

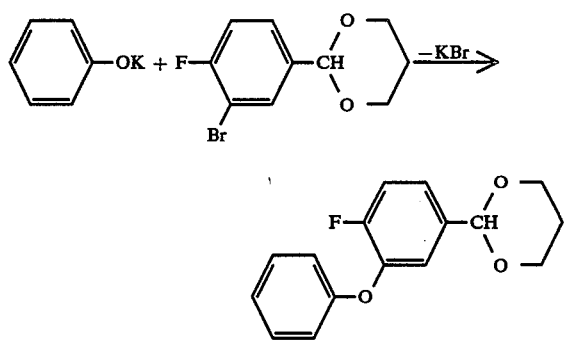

Alkali metal phenolates and alkaline earth metal phenolates which can be used as starting substances in process (2) are, for example, sodium phenolate, potassium phenolate and magnesium phenolate. Sodium phenolate is the preferred starting compound.

Copper or copper compounds are used as the catalysts. Examples of these catalysts which may be mentioned are copper, copper-(I) oxide, copper-(II) oxide, copper-(I) chloride and copper-(I) bromide.

Aprotic polar solvents are preferably used as the diluents in process (2). Examples of these solvents are dimethylformamide, dimethylacetamide, N-methylpyrrolidone, dimethylsulphoxide, tetramethylene sulphone, hexamethylphosphoric acid triamide and bis-(2-methoxyethyl) ether (diglyme). Diglyme is particularly preferred.

Auxiliaries from the series comprising alkali metal halides or carbonates and alkaline earth metal halides or carbonates are, for example, potassium carbonate and magnesium carbonate. These auxiliaries are preferably used if sodium phenolate is employed as the starting compound.

Basic dehydrating agents which can be used in process (2) are, for example, sodium hydroxide, potassium hydroxide, calcium hydroxide, potassium carbonate, sodium amide, sodium hydride and calcium hydride.

The reaction temperature is kept between 100° and 200° C., preferably between about 130° and 170° C., in process (2). The process is usually carried out under normal pressure.

About 1 to 1.5 mols, preferably about 1 to 1.2 mol of phenolate, about 0.01 to 0.5 mol, preferably about 0.1 to 0.5 mol, of copper catalyst, about 100 to 400 ml of diluent, if appropriate about 0.01 to 0.5 mol of an auxiliary from the series comprising alkali metal halides or carbonates and alkaline earth metal halides or carbonates and, if appropriate up to about 0.2 mol of a dehydrating agent are usually employed per mol of 3-bromo-4-fluoro-benzaldehyde acetal of the formula (II).

In a preferred embodiment of process (2), the phenolate is initially introduced in a diluent, to which, if appropriate, a dehydrating agent has been added, the copper catalyst and, if appropriate, the auxiliary from the series comprising alkali metal halides or carbonates and alkaline earth metal halides or carbonates are added and the mixture is heated up to the reaction temperature. the 3-bromo-4-fluoro-benzaldehyde acetal is then metered in the mixture is stirred until the reaction has ended. For working up, which can be effected by customary methods, the mixture is diluted, for example with toluene, and filtered and the solvent is distilled off from the filtrate under reduced pressure, whereupon the crude product remains as the residue.

The new compounds of the formula (I) can be used for the preparation of 4-fluoro-3-phenoxybenzaldehyde, which is known as an intermediate product for pyrethroids (see DE-OS (German Published Specification) No. 2,709,264). If 4-fluoro-3-phenoxy-benzaldehyde propyleneacetal is used, the preparation of 4-fluoro-3-phenoxy-benzaldehyde by splitting acetal compounds of the formula (I) with acids can be illustrated by the following equation:

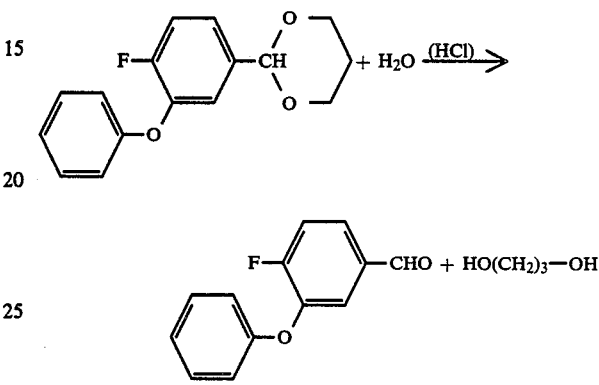

The splitting of the acetal for the preparation of 4-fluoro-3-phenoxy-benzaldehyde can be carried out by customary methods. In a preferred procedure, the selected compound of the formula (I) is dissolved in aqueous alcohol and the solution is left to stand at room temperature with a catalytic amount of a strong acid, for example hydrochloric acid. After some hours, a water-immiscible solvent, for example toluene, is added to the reaction mixture, the organic phase is separated off, washed with water, dried and filtered and the filtrate is distilled.

Formula (II) provides a definition of the new 3-bromo-4-fluoro-benzaldehyde acetals to be used as intermediate products. Preferably, in this formula, the radicals R individually represent $C_1$–$C_4$-alkyl or together represent $C_2$–$C_5$-alkanediyl, especially —$CH_2$—$CH_2$—. If propane-1,3-diol is used, the process described under (5) for the preparation of the new 3-bromo-4-fluoro-benzaldehyde acetals ("process (5)") can be outlined by the following equation:

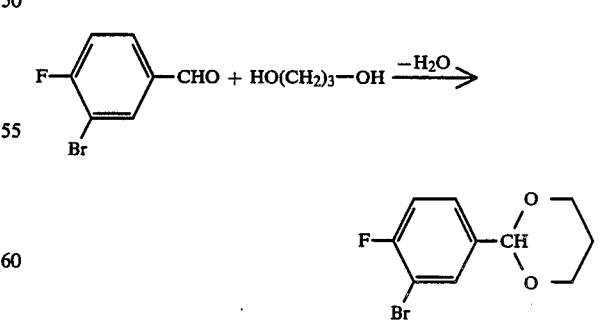

Alkanols or alkanediols which can be employed as acetalizing agents in process (5) are, for example, methanol, ethanol, propanol and butanol, and ethane-1,2-diol (ethylene glycol) and propane-1,3-diol. Ethylene glycol is the particularly preferred acetalizing component.

Suitable catalysts are, for example, hydrogen chloride, hydrogen bromide, sulphuric acid, p-toluenesulphonic acid, boron trifluoride, zinc chloride and acid ion exchange resins.

Suitable water-binding agents are, for example, orthoformic acid triethyl ester, dimethyl sulphite and chlorotrimethylsilane.

If appropriate, process (5) is carried out in the presence of a diluent. Suitable diluents are, in particular, solvents with which water can be removed from the reaction mixture by azeotropic distillation. Examples which may be mentioned are benzene, toluene and xylene.

The reaction temperature is between 0° and 150° C. in process (5), preferably between about 20° and 120° C. The process is in general carried out under normal pressure.

About 1 to 1.5 molar equivalents, preferably about 1 to 1.2 molar equivalents, of alkanol or alkanediol and, if appropriate, about 2 to 3 mols, preferably about 2 to 2.5 mols, of a water-binding agent are employed per mol of 3-bromo-4-fluoro-benzaldehyde.

In a preferred embodiment of process (5), 3-bromo-4-fluoro-benzaldehyde, the alkanol or alkanediol and a water-binding agent are mixed and the mixture is heated for some hours. For working up, which can be effected by customary methods, the mixture is diluted, for example, with a water-immiscible solvent, for example toluene, the solution is washed with ice-water, dried and filtered and the filtrate is distilled.

The process for the preparation of 3-bromo-4-fluoro-benzaldehyde from 3-bromo-4-fluoro-benzyl alcohol ("process (7)") is preferably carried out using a diluent. Possible diluents are, if appropriate, water and/or aliphatic or aromatic, optionally halogenated hydrocarbons, for example pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene.

The reaction temperature is between about 0° and 100° C., preferably between about 10° and 60° C., in process (7). The process is usually carried out under normal pressure.

In a preferred variant (a) of process (7), chromium-(VI) oxide/pyridine/hydrogen chloride (1/1/1) is used as the oxidizing agent. To a solution of this oxidizing agent, for example in methylene chloride, is added a solution of 3-bromo-4-fluoro-benzyl alcohol, also in methylene chloride, and the mixture is stirred until the reaction has ended. For working up, the mixture is distilled, if appropriate after decanting off undissolved components.

In a second preferred variant (b) of process (7), nitric acid is used as the oxidizing agent and water is used as the diluent. 3-Bromo-4-fluoro-benzyl alcohol is added to this and the mixture is stirred at room temperature for some hours. For working up, the mixture is rendered alkaline with sodium hydroxide solution and extracted with a water-immiscible solvent, for example toluene, the extract is washed with water, dried and filtered and the filtrate is distilled.

In a third preferred variant (c) of process (7), chromic acid or a mixture of dichromate and sulphuric acid is used as the oxidizing agent. In this case, the diluent is preferably a two-phase system of water and one of the abovementioned organic solvents. Compounds which are suitble for the transfer of anions from water into organic solvents are preferably used as catalysts. Examples of these compounds are benzyl-triethyl-ammonium bisulphate, tetrabutyl-ammonium bromide and methyl-tricapryl-ammonium chloride (Aliquat 336).

For carrying out process variant (7) (c), 3-bromo-4-fluoro-benzyl alcohol is initially introduced in an organic solvent, for example methylene chloride, and sulphuric acid, water, catalyst and dichromate are added. The reaction mixture is stirred for some hours. For working up, the mixture is diluted with water, the organic phase is separated off, washed with water, dried and filtered and the filtrate is distilled.

3-Bromo-4-fluoro-benzyl alcohol and a process for its preparation are the subject of German Patent Application No. P 2933985.3 filed Aug. 22nd 1979 Le A 19 875. This compound is obtained when 3-bromo-4-fluoro-benzoyl fluoride is reacted with a complex hydride, for example sodium tetrahydridoborate, if appropriate using a diluent, for example isopropanol, at temperatures between 0° and 50° C. The reaction mixture is stirred until the reaction has ended, and is diluted with ice-water and acidified. It is then extracted with a water-immiscible solvent, for example with methylene chloride, the extract is dried and filtered and the filtrate is distilled.

The 3-bromo-4-fluoro-benzoyl fluoride to be used as the starting compound is the subject of German Patent Application No. P 2,915,738 Le A 19 590. This compound is obtained when 4-chloro-benzoyl chloride is converted into 4-fluoro-benzoyl fluoride by reaction with potassium fluoride and the 4-fluoro-benzoyl fluoride is brominated to give 3-bromo-4-fluoro-benzoyl fluoride, according to the equation below:

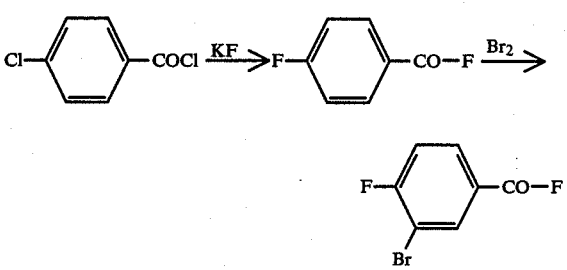

4-Chloro-benzoyl chloride is reacted with potassium fluoride, for example in tetramethylene sulphone, at temperatures between 200° and 220° C. and the reaction mixture is worked up by distillation. 4-Fluoro-benzoyl fluoride of boiling point 53° C./20 mbars (refractive index: $n_D^{20} = 1.4792$) is obtained.

4-Fluoro-benzoyl fluoride is reacted with elementary bromine in the presence of 1% of iron(III) chloride at 70° to 75° C. In the case of a batch of 1 mole, after distillation, 40 g of unchanged starting material are recovered and 182 g of a mixture of 3-bromo-4-fluoro-benzoyl fluoride (boiling point: 82°-83° C./15 mbars; refractive index: $n_D^{20} = 1.5315$; melting point: 32°-34° C.) and 3-bromo-4-fluoro-benzoyl bromide (boiling point: 123° C./15 mbars; melting point: 35°-37° C.) are obtained.

In principle, the 3-bromo-4-fluoro-benzaldehyde (III) to be prepared according to process (7) can also be obtained by other methods, for example by bromination of 4-fluoro-benzaldehyde or by side chain halogenation of 3-bromo-4-fluoro-toluene, followed by a Sommelet reaction.

PREPARATIVE EXAMPLES

EXAMPLE 1

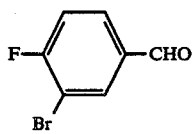

Variant (a)

A solution of 45.9 g (0.225 mol) of 3-bromo-4-fluoro-benzyl alcohol in 45 ml of methylene chloride was added dropwise to a suspension of 78 g of pyridine/-CrO₃/HCl in 450 ml of methylene chloride. During this addition, the temperature of the mixture rose to about 40° C. The mixture was then subsequently stirred for 1 hour, the organic phase was decanted from the chromium salts and the solvent was distilled off in vacuo. The residue was distilled. 39 g (86% of theory) of 3-bromo-4-fluoro-benzaldehyde with a boiling point of 63°-65° C./0.3 mm Hg were thus obtained.

Variant (b)

10.2 g (0.05 mol) of 3-bromo-4-fluoro-benzyl alcohol were added to a mixture of 10 g of nitric acid (density: 1.4) and 5 ml of water at 30°-35° C. and the mixture was then stirred at room temperature for 5 hours. After adding 30 g of ice, sodium hydroxide solution was added to the mixture until the pH value reached 13, and the mixture was then extracted by shaking with 200 ml of toluene. The organic phase was washed three times with 50 ml of water each time, dried over sodium sulphate and then evaporated. The residue was distilled. 6.1 g (60% of theory) of 3-bromo-4-fluoro-benzaldehyde were thus obtained in the form of an oil which slowly solidified and had a melting point of 29°-31° C.

Variant (c)

A mixture of 29.4 g (0.3 mol) of sulphuric acid, 50 ml of water and 2 ml of Aliquat 336 (tricapryl-methylammonium chloride) was added to a solution of 20.5 g (0.1 mol) of 3-bromo-4-fluoro-benzyl alcohol in 250 ml of methylene chloride at room temperature. Thereafter, 9.7 g (0.033 mol) of potassium dichromate were added to the reaction mixture and the temperature was kept at about 25° C. for 2 hours by cooling slightly. After adding 100 ml of water, the organic phase was separated off and the aqueous phase was extracted once more with 100 ml of methylene chloride. The organic phases were washed twice with 100 ml of water each time, then once with 100 ml of saturated sodium bicarbonate solution and once more with 100 ml of water, dried over sodium sulphate and evaporated in vacuo. The residue was distilled. 16.3 g (81% of theory) of 3-bromo-4-fluoro-benzaldehyde were obtained in this manner as a colorless oil with a boiling point of 65° C./0.3 mm Hg.

EXAMPLE 2

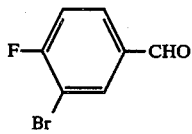

62 g of 4-fluoro-benzaldehyde were added dropwise to a mixture of 166 g of aluminum chloride and 150 ml of 1,2-dichloroethane at an internal temperature of 30° C. and the mixture was subsequently stirred for about 30 minutes. 88 g of bromine were then added dropwise at an internal temperature between 30° and 40° C. The reaction mixture was subsequently stirred for about 2 hours and then poured into ice. After separating off the organic phase, the aqueous phase was then extracted with 1,2-dichloroethane. The combined organic phases were washed with water, dried with sodium sulphate and filtered. After distilling off the solvent from the filtrate under reduced pressure, a crude product which, according to analysis by gas chromatography, contained 78.8% of 3-bromo-4-fluoro-benzaldehyde and 17.6% of 4-fluoro-benzaldehyde was obtained as the residue. After vacuum distillation, 58 g of 3-bromo-4-fluoro-benzaldehyde of boiling point 108° C./25 mbars and of refractive index $n_D^{20}$: 1.5737 were obtained. The product gradually solidified: melting point: 30°-31° C.

EXAMPLE 3

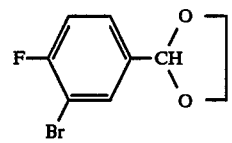

26 g (0.24 mol) of trimethylchlorosilane were added to a mixture of 20.3 g (0.1 mol) of 3-bromo-4-fluoro-benzaldehyde and 6.8 g (0.11 mol) of ethane-1,2-diol and the mixture was heated to 100° C. for 3 hours. After cooling to room temperature, 100 ml of toluene were added and the mixture was shaken twice with 50 ml of ice-water each time. The organic phase was dried over sodium sulphate and evaporated in vacuo. The residue was distilled in vacuo. 21 g (85% of theory) of 3-bromo-4-fluoro-benzaldehyde ethyleneacetal were thus obtained in the form of a colorless oil with a boiling point of 79°-81° C./0.1 mm Hg.

EXAMPLE 4

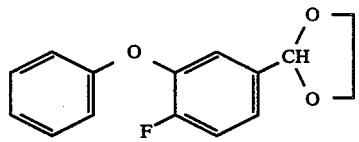

To dehydrate a suspension of 3.2 g (27.5 mmol) of sodium phenolate in 3 ml of diglyme, 0.1 g (3.5 mmol) of sodium hydride was added, and 0.05 g of copper(I) oxide (0.35 mmol) and 0.5 g (6.5 mmol) of potassium chloride were then added to the mixture. The reaction mixture was heated to 155° C. under an inert gas (for example argon), and 6.2 g (25 mmol) of 3-bromo-4-fluoro-benzaldehyde ethyleneacetal were added at this temperature. The mixture was subsequently stirred at 155° C. for 7 hours and, after cooling to room temperature, 50 ml of toluene were added and the inorganic material was filtered off. The filtrate was freed from solvent in vacuo. 6.0 g of a product containing 87% of 4-fluoro-3-phenoxy-benzaldehyde ethyleneacetal were thus obtained (corresponding to a yield of 80% of theory).

EXAMPLE 5

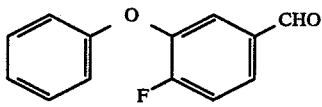

A solution of 26 g (0.1 mol) of 4-fluoro-3-phenoxy-benzaldehyde ethyleneacetal in 60 ml of ethanol, 20 ml of water and 1 ml of concentrated hydrochloric acid was stored at room temperature for 3 hours. The ethanol was then distilled off in vacuo, and 100 ml of toluene were added to the residue. The water was separated off and the organic phase was washed twice with 50 ml of water each time, dried over sodium sulphate and evaporated in vacuo. The residue was distilled in vacuo. 19.6 g (91% of theory) of 4-fluoro-3-phenoxy-benzaldehyde were obtained in this manner in the form of a colorless oil with a boiling point of 102°–104° C. /0.1 mm Hg.

It will be appreciated that the instant specification and examples are set forth by way of illustration and not limitation, and that various modifications and changes may be made without departing from the spirit and scope of the present invention.

What is claimed is:

1. A 4-fluoro-3-phenoxy-benzaldehyde acetal of the formula

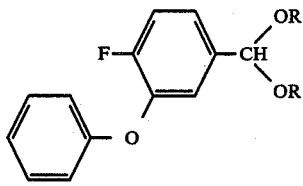

in which
the two radicals R each independently is $C_1$–$C_4$-alkyl or together are $C_2$–$C_5$-alkanediyl.

2. A compound according to claim 1, in which the radicals R together are ethanediyl.

* * * * *